United States Patent [19]

Milzner

[11] 4,402,730
[45] Sep. 6, 1983

[54] PYRIMIDINE DERIVATIVES AND THEIR USE AS HERBICIDES

[75] Inventor: Karlheinz Milzner, Basel, Switzerland

[73] Assignee: Sandoz Ltd., Basel, Switzerland

[21] Appl. No.: 225,046

[22] Filed: Jan. 14, 1981

[30] Foreign Application Priority Data

Jan. 25, 1980 [GB] United Kingdom ............... 8002573

[51] Int. Cl.$^3$ .................... A01N 43/54; C07D 239/24
[52] U.S. Cl. ........................................ 71/92; 544/320
[58] Field of Search ............................ 544/320; 71/92

[56] References Cited

U.S. PATENT DOCUMENTS 4,014,677  3/1977  Fischer .................................. 71/92
4,116,674  9/1978  Sonley et al. ......................... 71/92

FOREIGN PATENT DOCUMENTS 1523274  8/1978  United Kingdom .

*Primary Examiner*—Nicholas S. Rizzo
*Attorney, Agent, or Firm*—Gerald D. Sharkin; Richard E. Vila

[57] ABSTRACT

The invention provides 6-(2-propenyloxy)-4-methyl-2-aminopyrimidine derivatives which are chlorinated or brominated in 2 or 3 position of the 2-propenyl moiety, e.g. 6-(2-chloro-2-propenyloxy)-4-methyl-2-n-hexylaminopyrimidine. The compounds are useful as herbicides and allow the control of undesired weeds in a crop locus.

18 Claims, No Drawings

PYRIMIDINE DERIVATIVES AND THEIR USE AS HERBICIDES

The present invention relates to pyrimidinyl ethers possessing herbicidal properties.

More specifically, the present invention provides compounds of formula I

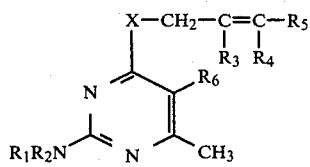

wherein
X is O or S
either
R$_1$ is C$_1$-C$_{18}$alkyl; C$_1$-C$_{18}$alkyl substituted by up to 2 substituents selected from C$_1$-C$_4$alkoxy or 2-tetrahydrofuryl; C$_3$-C$_8$cycloalkyl or C$_3$-C$_8$cycloalkyl-C$_1$-C$_5$alkyl unsubstituted or substituted by up to 2 halogens having an atomic weight of 9 to 35; or is C$_1$-C$_{18}$alkenyl and
R$_2$ is H or C$_1$-C$_5$alkyl,
or
R$_1$ and R$_2$ together are a C$_4$-C$_6$alkylene chain,
R$_3$ and R$_4$ and R$_5$ are each, independently, H, Cl, Br or C$_1$-C$_4$alkyl and
R$_6$ is H or C$_1$-C$_5$alkyl,
with the proviso that at least one of R$_3$, R$_4$ and R$_5$ is halogen.

Any alkyl in the compounds of formula I may be straight or branched.

If R$_1$ is C$_1$-C$_{18}$alkyl, it is e.g. C$_1$-C$_{12}$alkyl, preferably C$_1$-C$_{10}$alkyl, more preferably C$_3$-C$_7$alkyl, particularly n-C$_6$H$_{13}$, n-C$_4$H$_9$, i-C$_3$H$_7$, 2-C$_4$H$_9$ or 3-CH$_3$-2-butyl.

If R$_1$ is the above defined substituted C$_1$-C$_{18}$alkyl, it is preferably substituted by CH$_3$O or 2-tetrahydrofuryl, and particularly mono-substituted.

Where R$_1$ is or contains C$_3$-C$_8$-cycloalkyl, this is preferably C$_3$-C$_6$cycloalkyl, more preferably C$_3$-C$_5$cycloalkyl.

Where R$_1$ is C$_3$-C$_8$cycloalkyl-C$_1$-C$_5$alkyl the alkylene moiety thereof has preferably 1 to 3 carbon atoms and is more preferably CH$_2$.

Where R$_1$ is C$_3$-C$_8$cycloalkyl or C$_3$-C$_8$cycloalkyl-C$_1$-C$_5$alkyl substituted by halogen, the halogen is preferably Cl or Br, particularly Cl and is preferably in the cycloalkyl moiety of the group.

Where R$_1$ is C$_1$-C$_{18}$alkenyl, it may be branched or straight chained and is preferably C$_1$-C$_{12}$alkenyl.

When any of R$_3$, R$_4$ and R$_5$ is C$_1$-C$_4$alkyl, it is preferably ethyl or methyl, particularly the latter.

Preferred compounds of formula I have one or more of the following features:
(a) X is O;
(b) R$_2$ is H or CH$_3$, particularly H;
(c) R$_3$ is H, Cl or Br, particularly Cl;
(d) R$_4$ is H or C$_1$-C$_4$alkyl;
(e) R$_5$ is H, Cl or Br;
(f) R$_6$ is H.

A preferred sub-group of the compounds of formula I is represented by formula Ia,

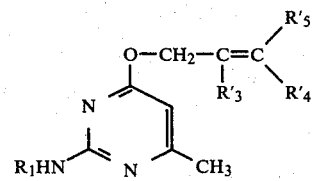

wherein
R$_1$ is as defined above,
R$_3'$ is H, Cl or Br
R$_4'$ is H or CH$_3$
R$_5'$ is H, Cl or Br
whereby either R$_3'$ or R$_5'$ is Cl or Br.

The present invention also provides a process for producing a compound of formula I which comprises etherifying a compound of formula II

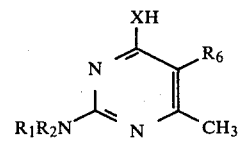

wherein X, R$_1$, R$_2$ and R$_6$ are as defined above, with a compound of formula III

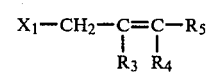

wherein
X$_1$ is a leaving group capable of being split off under the reaction conditions and
R$_3$, R$_4$ and R$_5$ are as defined above.

The compounds of formula I may be prepared and used in the form of acid addition salts. Any salt form of compounds of formula I is preferably in the form of an agriculturally acceptable salt form. The acid addition salt forms can be prepared from the free base form in conventional manner and vice versa.

The above process may be carried out in conventional manner under conditions known for the preparation of 4-pyrimidinyl ethers.

X$_1$ can be any leaving group displaceable under 4-hydroxy-pyrimidine condensing reaction conditions and is preferably halogen, particularly chlorine.

The reaction may be carried out in the absence or presence of a solvent, preferably in a solvent. Where a solvent is used, such is preferably an amide of an organic carboxylic acid such as dimethylformamide, a hydrocarbon, a chlorinated hydrocarbon, an ether or ketone, an alcohol or pyridine. A suitable reaction temperature is from 0° to 150° C., preferably from 40° to 120° C. The reaction is preferably carried out in the presence of an acid binding agent such as potassium or sodium carbonate, potassium hydroxide, sodium methoxide, triethylamine or pyridine.

The compounds used as starting material are either known or may be produced by conventional manner. So the compounds of formula II may be obtained by condensing 5-methylisothiourea with an acetyl acetic acid ester and reacting the so obtained 2-methylthio-4-hydroxy-6-methylpyrimidine with an amine to form the desired compound of formula II.

Geometric isomerism is possible in compounds of formula I in which $R_3$ is different of $R_4$ and/or $R_5$ (and where $R_3$ does not together with $R_4$ form a covalent bond). The particular geometric forms of such intermediates and starting materials are generally unaffected by the reaction conditions described herein and will appear in the final products. When mixtures of geometric isomers are produced, it is, as a practical matter, generally preferred to employ such mixtures as such in the herbicide method and compositions of the invention, even though separation may be effected by known procedures.

The compounds of formula I are useful because they affect the plant growth. In particular, they are indicated for use in the control of undesired plant growth in view of the damage caused to a wide range of both monocotyledoneous and dicotyledoneous plants including for example *Lepidium sativum, Avena fatua, Agrostis alba* and *Lolium perenne* by test dosages equivalent to an application rate of 0.2 to 5.0 kg/ha. They are effective when applied pre- or post-emergence, with post-emergence application being generally preferred. In view of their herbicidal effect the compounds of formula I are indicated for use in combatting weeds, e.g. dicotyledoneous weeds such as *Amaranthus retroflexus, Capsella bursa-pastoris, Chenopodium alba, Stellaria media, Senecio vulgaris* and *Galium aparine* and, especially, grassy weeds such as *Agrostis alba, Alopecurus myosuroides, Apera spica venti, Avena fatua, Echinochloa crus-galli, Lolium perenne, Digitaria sanguinalis, Setaria italica* and *Panicum spp.*

The present invention therefore also provides a method of combatting weeds. The amount to be applied to attain the desired effect will vary depending on the plants involved and other standard variables such as the compound employed, mode of application, conditions of treatment and the like. The appropriate application rates can be determined by routine procedures by those skilled in the art and will, in general, lie in the range of from about 0.2 to 7 kg/ha, preferably from about 0.5 to 5 kg/ha, more preferably from 1.0 to 3.0 kg/ha.

The compounds of formula I are relatively less phytotoxic towards crops than towards weeds. Said selective herbicidal activity of the compounds of formula I is, for example, noted after pre-emergence application in a crop locus including small grain crops (such as wheat, paddy rice) sugar beet, potato sunflower and cotton. The pre-emergence selective herbicidal activity is particularly effective in a cotton, potato or sunflower locus, especially in cotton. The selective herbicidal effect of the compounds of formula I is also noted after post-emergence application to a crop locus including i.a. potato and a small grain crop such as wheat, barley, upland rice and paddy rice (flooded rice). This post-emergence selective herbicidal activity is particularly effective in paddy rice.

For use as a selective herbicide in a crop locus, the application rate will naturally also depend on the crop involved, but in general, satisfactory results will be obtained with a rate of 0.2 to 5.0 kg, preferably 1.0 to 3.0 kg of a compound of formula I per hectare.

The present invention therefore also provides a method of combatting weeds in a crop locus as mentioned above, particularly in paddy rice or wheat which comprises applying to the locus a compound of formula I in an amount sufficient to severely damage or kill the weeds, without substantially damaging the crop.

The emergence time referred to above is with respect to the weeds. In the preferred post-emergence selective use, the compounds of formula I may be applied pre-emergence the crops, but it is generally preferred to effect the application post-emergence both the weeds and crop.

The compounds may be and preferably are employed as herbicidal compositions in association with herbicide carriers or diluents, comprising e.g. from 0.01 to about 80% by weight of a compound of formula I. Such compositions also form part of the present invention. They are obtained analogous to known procedures by mixing the active agents with the carriers or diluents. Suitable formulation forms of the compositions according to the invention are application forms, e.g. a spray liquor and concentrates e.g. a liquid emulsifiable concentrate, a granulate or a wettable powder. Solid forms, e.g. dusting forms and granulates, may be produced by mixing or impregnating solid herbicide carriers such as diatomaceous earth, kaolin, talc, chalk, limestone and cellulose powder, with the compounds.

Additives may be employed in the herbicidal composition. Typical of such additives are wetting and dispersing agents, e.g. the condensation product of formaldehyde with naphthalene sulphonate and alkyl benzene sulphonates, adhesion imparting agents, e.g. dextrin, and emulsion stabilizers, e.g. ammonium caseinate. Such additives are suitable for incorporation into, e.g. a wettable powder form of composition or together with suitable solvents, e.g. hydrocarbons such as benzene, alcohols such as isopropanol form emulsion concentrates.

Concentrate forms of composition generally contain between 2 and 80%, preferably between 2 and 50%, by weight of a compound of formula I as active agent.

Application forms of composition generally contain between 0.01 and 10% by weight of a compound of formula I as active agent.

Insofar as the production of any starting material is not particularly described, these compounds are known, or may be produced in accordance with or in a manner analogous to known processes.

Specific Examples of herbicidal compositions will now be described.

EXAMPLE A

Wettable Powder

25 Parts of a compound of formula I, e.g. the compound of Example 1, hereinafter given, 5 parts of a condensation product from formaldehyde and naphthalene sulphonate, 2 parts of an alkyl benzene sulphonate, 5 parts dextrin, 1 part of ammonium caseinate and 62 parts of diatomaceous earth are mixed until a homogeneous mixture is obtained and then ground until the particles are considerably smaller than 45 microns as an average.

EXAMPLE B

Emulsion Concentrate

25 Parts of a compound of formula I, e.g. the compound of Example 1, hereinafter given, 65 parts of xylene, 10 parts of the mixed reaction product of an alkylphenol with ethylene oxide and calcium-dodecylbenzene sulphonate are thoroughly mixed until a homogeneous solution is obtained. The resulting emulsion concentrate is diluted with water before use.

EXAMPLE C

Granulate

5 Kg of a compound of formula I, e.g. the compound of Example 1, hereinafter given, are dissolved in 25 l methylene chloride. The solution is then added to 95 kg of granulated attapulgate (mesh size 24/48 mesh/inch) and thoroughly mixed. The solvent is then evaporated off under reduced pressure with warming.

The invention is further illustrated by the following Examples wherein temperatures are in °C.

EXAMPLE 1

6-(2-Chloro-2-propenyloxy)-4-methyl-2-n-hexylamino-pyrimidine 42.0 g 6-Hydroxy-4-methyl-2-n-hexylamino-pyrimidin (0.2 Mol), 27.6 g $K_2CO_3$ (0.2 Mol), 24.4 g 2,3-dichloro-1-propene (0.22 Mol) and 150 ml dimethylformamide are charged in a sulphonation flask. The mixture is heated for about 3 hours at a bath temperature of 110°, then cooled to room temperature and thereafter poured in 500 ml water. This mixture is extracted with ether, the ether extract dried with $Na_2SO_4$ and concentrated with the aid of a flask rotary vacuum evaporator at a temperature of up to 60°. The impure title compound is obtained as a brown oil, which is purified chromatographically with ether/hexane 1:3 on silicagel to give a yellow oil that slowly crystallises. m.p. 36°–37°.

Following the procedure of Example 1 but employing appropriate pyrimidine compounds of formula II and propene derivatives of formula III the following compounds of formula I are obtained (where the compounds are obtained as an oil, their Rf value on silica gel is given whereby (a), (b), (c) and (d) specify the eluant used which is for (a) diethylether:n-hexane 1:1, for (b) diethylether; for (c) diethylether:n-hexane 1:3 and for (d) n-pentane:diethylether 3:1).

TABLE I (Compounds of formula I wherein $R_6 =$ H)

| Example No. | $NR_1R_2$ | $-X-CH_2-\underset{R_3}{C}=\underset{R_4}{C}-R_5$ | m.p./ Rf |
|---|---|---|---|
| 2 | $-NHCH_3$ | $-OCH_3C(Cl)=CH_2$ | 92–93 |
| 3 | $-NHn-C_3H_7$ | $-OCH_2C(Cl)=CH_2$ | 63–64 |
| 4 | $-NHn-C_3H_7$ | $-OCH_2CH=CHCl$ (c/t) | 51–54 |
| 5 | $-NHn-C_3H_7$ | $-OCH_2C(Cl)=CHCl$ | 46–48 |
| 6 | $-NHn-C_3H_7$ | $-OCH_2C(Br)=CH_2$ | 64–65 |
| 7 | $-NH(CH_2)_3OCH_3$ | $-OCH_2C(Cl)=CH_2$ | 50–51 |
| 8 | $-NHi-C_3H_7$ | $-OCH_2C(Cl)=CH_2$ | (a) 0.25[(1)] |
| 9 | $-NHi-C_3H_7$ | $-OCH_2CH=CHCl$ (c/t) | (a) 0.10 |
| 10 | $-NHi-C_3H_7$ | $-OCH_2CH=C(Cl)-CH_3$ (c/t) | (a) 0.25 |
| 11 | $-NHi-C_3H_7$ | $-OCH_2C(Br)=CH_2$ | (a) 0.25 |
| 12 | $-NH-n-C_4H_9$ | $-OCH_2C(Cl)=CH_2$ | 53–55 |
| 13 | $-NH-n-C_4H_9$ | $-OCH_2C(Br)=CH_2$ | 50–51 |
| 14 | $-NH-n-C_4H_9$ | $-OCH_2CH=CHCl$ (c/t) | 38–40 |
| 15 | $-NH-i-C_4H_9$ | $-OCH_2C(Cl)=CH_2$ | 59–61 |
| 16 | $-NH-i-C_4H_9$ | $-OCH_2CH=CHCl$ (c/t) | 48–50 |
| 17 | $-NH-sec-C_4H_9$ | $-OCH_2C(Cl)=CH_2$ | (b) 0.45 |
| 18 | $-NH-sec-C_4H_9$ | $-OCH_2CH=CHCl$ (c/t) | (a) 0.25 |
| 19 | $-NH-sec-C_4H_9$ | $-OCH_2C(Br)=CH_2$ | (a) 0.25 |
| 20 | $-NH-n-C_6H_{13}$ | $-OCH_2CH=CHCl$ (c/t) | 32–34 |
| 21 | $-NH-cyclohexyl$ | $-OCH_2C(Cl)=CH_2$ | (b) 0.55 |
| 22 | $-NH-n-C_{12}H_{25}$ | $-OCH_2C(Cl)=CH_2$ | 36–37 |
| 23 | -pyrrolidinyl | $-OCH_2C(Cl)=CH_2$ | (a) 0.35 |
| 24 | 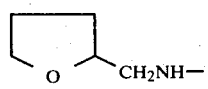 | $-OCH_2C(Cl)=CH_2$ | 49 |
| 25 | $-NHCH(CH_3)CH_2OCH_3$ | $-OCH_2CH=CHCl$ | (a) 0.25 |
| 26 | $-NHCH(CH_3)CH_2OCH_3$ | $-OCH_2C(Cl)=CH_2$ | (a) 0.30 |
| 27 | $-NHCH(CH_3)CH_2OCH_3$ | $-OCH_2CH=C(Cl)CH_3$ | (a) 0.34 |
| 28 | $-NHCH(CH_3)CH_2OCH_3$ | $-OCH_2C(Br)=CH_2$ | (a) 0.26 |
| 29 | $-NH-cyclopentyl$ | $-OCH_2CH=CHCl$ | (a) 0.36 |
| 30 | $-NH-cyclopentyl$ | $-OCH_2C(Cl)=CH_2$ | (a) 0.47 |
| 31 | $-NH-n-C_6H_{13}$ | $-OCH_2C(Br)=CH_2$ | 38–40 |
| 32 | $-NH-n-C_6H_{13}$ | $-OCH_2CH=C(Cl)CH_3$ | 46–48 |
| 33 | $-NH-cyclopropyl$ | $-OCH_2CH=CHCl$ | (a) 0.34 |
| 34 | $-NH-cyclopropyl$ | $-OCH_2-C(Cl)=CH_2$ | (a) 0.37 |
| 35 | $-NH-CH_2CH_2OCH_3$ | $-OCH_2CH=CHCl$ | 59–63 |
| 36 | $-NH-CH_2CH_2OCH_3$ | $-OCH_2C(Cl)=CH_2$ | 63–65 |
| 37 | $-NH-CH_2CH_2OCH_3$ | $-OCH_2C(Br)=CH_2$ | 71–73 |
| 38 | $-NH-n-C_3H_7$ | $-OCH_2CH=CHCl$ (c/t) | 51–54 |
| 39 | $-NHC_4H_{9-n}$ | $-OCH_2CH=C(Cl)CH_3$ (c/t) | 43–45 |
| 40 | $-NHC_4H_{9-iso}$ | $-OCH_2C(Br)=CH_2$ | 58–60 |
| 41 | $-NHC_4H_{9-sec}$ | $-OCH_2CH=C(Cl)CH_3$ (c/t) | (a) 0.25 |
| 42 | $-NHC_4H_{9-tert.}$ | $-OCH_2C(Cl)=CH_2$ | (a) 0.30 |
| 43 | $-NHC_5H_{11-n}$ | $-OCH_2C(Cl)=CH_2$ | 49–51 |
| 44 | $-NHC_5H_{11-n}$ | $-OCH_2C(Br)=CH_2$ | 44–45 |
| 45 | $-NHC_5H_{11-n}$ | $-OCH_2CH=CHCl$ (c/t) | 59–61 |
| 46 | $-NHC_5H_{11-n}$ | $-OCH_2CH=C(Cl)CH_3$ (c/t) | 47–49 |
| 47 | $-NHC_5H_{11-iso}$ | $-OCH_2C(Cl)=CH_2$ | 76–78 |
| 48 | $-NHC_5H_{11-iso}$ | $-OCH_2C(Br)=CH_2$ | 70–72 |

TABLE I-continued (Compounds of formula I wherein $R_6 = H$)

| Example No. | $NR_1R_2$ | $-X-CH_2-\underset{R_3}{C}=\underset{R_4}{C}-R_5$ | m.p./Rf |
|---|---|---|---|
| 49 | $-NHC_5H_{11}\text{-}iso$ | $-OCH_2CH=CHCl$ (c/t) | 53–55 |
| 50 | $-NHC_5H_{11}\text{-}iso$ | $-OCH_2CH=C(Cl)CH_3$ (c/t) | 66–68 |
| 51 | $-NHCH(CH_3)CH_2CH_2CH_3$ | $-OCH_2C(Cl)=CH_2$ | (a) 0.30 |
| 52 | $-NHCH(CH_3)CH_2CH_2CH_3$ | $-OCH_2C(Br)=CH_2$ | (a) 0.30 |
| 53 | $-NHCH(CH_3)CH_2CH_2CH_3$ | $-OCH_2CH=CHCl$ (c/t) | (a) 0.30 |
| 54 | $-NHCH(CH_3)CH_2CH_2CH_3$ | $-OCH_2CH=(Cl)CH_3$ (c/t) | (a) 0.25 |
| 55 | $-NHCH(CH_3)CH(CH_3)_2$ | $-OCH_2C(Cl)=CH_2$ | (c) 0.20 |
| 56 | $-NHCH(CH_3)CH(CH_3)_2$ | $-OCH_2C(Br)=CH_2$ | (c) 0.15 |
| 57 | $-NHCH(CH_2CH_3)_2$ | $-OCH_2C(Cl)=CH_2$ | (a) 0.25 |
| 58 | $-NHCH(CH_2CH_3)_2$ | $-OCH_2C(Br)=CH_2$ | (c) 0.15 |
| 59 | $-NHCH(CH_2CH_3)_2$ | $-OCH_2CH=CHCl$ (c/t) | (c) 0.15 |
| 60 | $-NH-$cyclopentyl | $-OCH_2C(Br)=CH_2$ | (a) 0.25 |
| 61 | $-NH-$cyclopentyl | $-OCH_2CH=C(Cl)CH_3$ (c/t) | (a) 0.25 |
| 62 | $-NHCH(CH_3)CH_2C_3H_{7}\text{-}iso$ | $-OCH_2C(Cl)=CH_2$ | (a) 0.35 |
| 63 | $-NHCH(CH_3)CH_2C_3H_{7}\text{-}iso$ | $=OCH_2C(Br)=CH_2$ | (a) 0.35 |
| 64 | $-NH-$cyclohexyl | $-OCH_2C(Br)=CH_2$ | (a) 0.30 |
| 65 | $-NH-$cyclohexyl | $-OCH_2CH=CHCl$ (c/t) | (a) 0.25 |
| 66 | $-NH-$cyclohexyl | $-OCH_2CH=C(Cl)CH_3$ (c/t) | (a) 0.25 |
| 67 | $-NHCH_2-$cyclohexyl | $-OCH_2C(Cl)=CH_2$ | 63–65 |
| 68 | $-NHCH_2-$cyclohexyl | $-OCH_2C(Br)=CH_2$ | 74–76 |
| 69 | $-NHC_7H_{15}\text{-}n$ | $-OCH_2(Cl)=CH_2$ | 36–38 |
| 70 | $-NHC_7H_{15}\text{-}n$ | $-OCH_2C(Br)=CH_2$ | 38–40 |
| 71 | $-NHC_7H_{15}\text{-}n$ | $-OCH_2CH=CHCl$ (c/t) | (a) 0.30 |
| 72 | $-NHC_7H_{15}\text{-}n$ | $-OCH_2CH=C(Cl)CH_3$ (c/t) | (c) 0.25 |
| 73 | $-NHCH(CH_3)C_5H_{11}\text{-}n$ | $-OCH_2C(Cl)=CH_2$ | (a) 0.35 |
| 74 | $-NHCH(CH_3)C_5H_{11}\text{-}n$ | $-OCH_2C(Br)=CH_2$ | (a) 0.35 |
| 75 | $-NHCH(CH_3)C_5H_{11}\text{-}n$ | $-OCH_2CH=CHCl$ (c/t) | (a) 0.35 |
| 76 | $-NHCH(CH_3)C_5H_{11}\text{-}n$ | $-OCH_2CH=C(Cl)CH_3$ (c/t) | (c) 0.15 |
| 78 | $-NHCH(CH_3)CH_2CH_2C_3H_{7}\text{-}i$ | $-OCH_2C(Br)=CH_2$ | (c) 0.15 |
| 79 | $-NHCH(C_3H_{7}\text{-}i)_2$ | $-OCH_2C(Cl)=CH_2$ | (c) 0.20 |
| 80 | $-NHCH(C_3H_{7}\text{-}iso)_2$ | $-OCH_2C(Br)=CH_2$ | (c) 0.20 |
| 81 | $-NHC_8H_{17}\text{-}n$ | $-OCH_2C(Cl)=CH_2$ | 29–31 |
| 82 | $-NHC_8H_{17}\text{-}n$ | $-OCH_2C(Br)=CH_2$ | 25–27 |
| 83 | $-NHCH(CH_3)C_6H_{13}\text{-}n$ | $-OCH_2C(Cl)=CH_2$ | (a) 0.25 |
| 84 | $-NHCH(CH_3)C_6H_{13}\text{-}n$ | $-OCH_2C(Br)=CH_2$ | (a) 0.35 |
| 85 | $-NHCH(CH_2)_3C_3H_{7}\text{-}i$ <br> $\quad\quad\quad\|$ <br> $\quad\quad\ CH_3$ | $-OCH_2C(Cl)=CH_2$ | (c) 0.20 |
| 86 | $-NHCH(CH_2)_3C_3H_{7}\text{-}i$ <br> $\quad\quad\quad\|$ <br> $\quad\quad\ CH_3$ | $-OCH_2C(Br)=CH_2$ | (a) 0.25 |
| 87 | $-NHCH_2CH-C_4H_{9}\text{-}n$ <br> $\quad\quad\quad\ \|$ <br> $\quad\quad\quad\ C_2H_5$ | $-OCH_2C(Cl)=CH_2$ | (c) 0.15 |
| 88 | $\quad\quad\ C_2H_5$ <br> $\quad\quad\quad\ \|$ <br> $-NHCH_2CH=C_4H_{9}\text{-}n$ | $-OCH_2C(Br)=CH_2$ | (a) 0.35 |
| 89 | $-NHCH_2CH-C_4H_{9}\text{-}n$ <br> $\quad\quad\quad\ \|$ <br> $\quad\quad\quad\ C_2H_5$ | $-OCH_2CH=C(Cl)CH_3$ (c/t) | (d) 0.15 |
| 90 | $-NHC_9H_{19}\text{-}n$ | $-OCH_2C(Cl)=CH_2$ | 43–44 |
| 91 | $-NHC_9H_{19}\text{-}n$ | $-OCH_2C(Br)=CH_2$ | (d) 0.15 |
| 92 | $-NHC_9H_{19}\text{-}n$ | $-OCH_2CH=CHCl$ (c/t) | (a) 0.25 |
| 93 | $-NHC_9H_{19}\text{-}n$ | $-OCH_2CH=C(Cl)CH_3$ (c/t) | (a) 0.25 |
| 94 | $-NHC_{10}H_{21}\text{-}n$ | $-OCH_2C(Cl)=CH_2$ | 28–30 |
| 95 | $-NHC_{10}H_{21}\text{-}n$ | $-OCH_2C(Br)CH_2$ | (a) 0.30 |
| 96 | $-NHC_{10}H_{21}\text{-}n$ | $-OCH_2CH=CHCl$ (c/t) | (a) 0.25 |
| 97 | $-NHC_{10}H_{21}\text{-}n$ | $-OCH_2CH=C(Cl)CH_3$ (c/t) | (a) 0.35 |
| 98 | $-NHC_{11}H_{23}\text{-}n$ | $-OCH_2C(Cl)=CH_2$ | 39–41 |
| 99 | $-NHC_{11}H_{23}\text{-}n$ | $-OCH_2C(Br)=CH_2$ | (a) 0.25 |
| 100 | $-NHC_{12}H_{25}\text{-}n$ | $-OCH_2C(Br)=CH_2$ | 36–38 |
| 101 | $-NHC_{12}H_{25}\text{-}n$ | $-OCH_2CH=CHCl$ (c/t) | 44–46 |
| 102 | $-NHC_{12}H_{25}\text{-}n$ | $-OCH_2CH=C(Cl)CH_3$ (c/t) | (c) 0.15 |
| 103 | $-NHC_{18}H_{37}\text{-}n$ | $-OCH_2C(Cl)=CH_2$ | 51–53 |
| 104 | $-NHC_{18}H_{37}\text{-}n$ | $-OCH_2C(Br)=CH_2$ | 51–53 |
| 105 | $-NHCH_2(CH_2)_7CH=CHC_8H_{17}\text{-}n$ | $-OCH_2C(Cl)=CH_2$ | (a) 0.35 |
| 106 | $-NHCH_2(CH_2)_7CH=CHC_8H_{17}\text{-}n$ | $-OCH_2C(Br)=CH_2$ | (a) 0.35 |

TABLE I-continued (Compounds of formula I wherein $R_6$ = H)

| Example No. | $NR_1R_2$ | $-X-CH_2-\underset{R_3}{C}=\underset{R_4}{C}-R_5$ | m.p./Rf |
|---|---|---|---|
| 107 | —NHCH$_2$—(tetrahydrofurfuryl) | —OCH$_2$C(Br)=CH$_2$ | 50–52 |
| 108 | -pyrrolidinyl | —OCH$_2$C(Br)=CH$_2$ | (c) 0.35 |
| 109 | -pyrrolidinyl | —OCH$_2$CH=C(Cl)CH$_3$ (c/t) | (c) 0.25 |
| 110 | —NHCH(CH$_3$)CH(CH$_3$)$_2$ | —OCH$_2$CH=CHCl (c/t) | (a) 0.25 |
| 111 | —NHCH(CH$_3$)CH(CH$_3$)$_2$ | —OCH$_2$CH=C(Cl)CH$_3$ (c/t) | Oil b.p. 0.05 = 145° C. |
| 112 | —NHiC$_3$H$_7$ | —SCH$_2$C(Cl)=CH$_2$ | (a) 0.30 |
| 113 | —NHnC$_6$H$_{13}$ | —SCH$_2$C(Cl)=CH$_2$ | (c) 0.10 (m.p. ~30°) |
| 114 | —NHCH(CH$_3$)CH$_2$CH(CH$_3$)$_2$ | —OCH$_2$—C=Cl—CH$_3$ (c/t) | Oil b.p. 0.02 = 153° C. |
| 115 | —NHnC$_8$H$_{17}$ | —OCH$_2$—CH=CHCl (c/t) | (a) 0.25 (m.p. 30°) |
| 116 | —NHnC$_8$H$_{17}$ | —OCH$_2$—CH=CCl—CH$_3$ (c/t) | (a) 0.25 (m.p. 30°) |
| 117 | —NHCH(iC$_3$H$_7$)$_2$ | —OCH$_2$CH=CHCl (c/t) | (a) 0.25 |
| 118 | —NHCH(iC$_3$H$_7$)$_2$ | —OCH$_2$CH=CCl—CH$_3$ (c/t) | (a) 0.25 |
| 119 | —NHCH(CH$_3$)CH$_2$CH(CH$_3$)$_2$ | —OCH$_2$CH=CHCl (c/t) | (a) 0.30 |
| 120 | —NHCH(CH$_3$)nC$_6$H$_{13}$ | —OCH$_2$CH=CHCl (c/t) | (a) 0.35 |
| 121 | —NHCH(CH$_3$)nC$_6$H$_{13}$ | —OCH$_2$CH=CCl—CH$_3$ (c/t) | (a) 0.35 |
| 122 | —NH—CH$_2$—(2,2-dichlorocyclopropyl) | —OCH$_2$CBr=CH$_2$ | 76–77 |
| 123 | —NH—CH$_2$—(2,2-dichlorocyclopropyl) | —OCH$_2$—CCl=CH$_2$ | 68–70 |

(1) the oxalate salt thereof having a m.p. of 99–101° and the sulfate salt a m.p. of 100–101°

TABLE 2

Compounds of formula I ($R_6 \neq$ H)

| Example No. | $NR_1R_2$ | $X-CH_2-\underset{R_3}{C}=\underset{R_4}{C}-R_5$ | $R_6$ | m.p./Rf |
|---|---|---|---|---|
| 124 | —NHC$_3$H$_{7\text{-}i}$ | —OCH$_2$C(Cl)=CH$_2$ | —CH$_3$ | (c) 0.10 |
| 125 | —NHC$_3$H$_{7\text{-}i}$ | —OCH$_2$C(Br)=CH$_2$ | —CH$_3$ | (a) 0.25 |
| 126 | —NHC$_3$H$_{7\text{-}i}$ | —OCH$_2$C(Cl)=CH$_2$ | —C$_3$H$_{7\text{-}n}$ | (a) 0.30 |
| 127 | —NHC$_3$H$_{7\text{-}i}$ | —OCH$_2$C(Br)=CH$_2$ | —C$_3$H$_{7\text{-}n}$ | (a) 0.25 |
| 128 | —NHC$_3$H$_{7\text{-}i}$ | —OCH$_2$CH=C(Cl)CH$_3$ | —C$_3$H$_{7\text{-}n}$ | (a) 0.25 |
| 129 | —NHC$_3$H$_{7\text{-}i}$ | —OCH$_2$CH=CHCl (c/t) | —C$_3$H$_{7\text{-}n}$ | (a) 0.25 |
| 130 | —NHC$_3$H$_{7\text{-}i}$ | —OCH$_2$C(Cl)=CH$_2$ | —C$_3$H$_{7\text{-}iso}$ | (c) 0.10 | c/t = cis/trans mixture

Starting Materials

The 2,3-dichloro-1-propene used as starting material in Example 1 may be obtained by addition of 10.6 mol Cl$_2$ to 10 mol allylchloride, and treatment of the so obtained 1,2,3-trichloropropane (10 mol) with KOH (16 Mol).

The 6-hydroxy-4-methyl-2-n-hexylamino-pyrimidine used as starting material may be obtained by reaction of thiourea (20 Mol) with dimethylsulphate (11 Mol) to form 5-methyl-isothiourea sulphate, followed by condensation of this reaction product (14 Mol) with CH$_3$COCH$_2$CO$_2$C$_2$H$_5$ (14 Mol) and reaction of the so obtained 6-hydroxy-4-methyl-2-methylthio-pyrimidine (0.5 Mol) with n-hexylamine (0.5 Mol) in ethanol (250 ml) in an autoclave (40 hours; bath temp. 160°).

HERBICIDAL ACTIVITY TESTS

TEST 1

Pre-emergence Greenhouse Treatment

Seed dishes measuring 30×40 cm are filled to a depth of 6 cm with a mixture of peat culture and sand. The exposed surface of the peat culture and sand mixture is sprayed with 50 ml of an aqueous suspension of herbicide (in the emulsion concentrate form of Example B), and seeds of *Lepidium sativum*, *Agrostis alba*, *Avena fatua* and *Lolium perenne* are then sown in each dish.

The number of seeds sown for each plant species depends on the seed germination potential and also the initial growth size of the particular seed plant. After sowing of the seeds, the treated surface is covered with a thin layer about 0.5 cm deep of the peat culture and sand mixture.

The prepared seed dishes are kept for 28 days at a temperature of 20° to 24° C. and 14 to 17 hours normal summer daylight each day.

Determination of the herbicidal effect of the particular herbicide is made after the 28 day period. The determination involves a visual evaluation of the degree and quality of damage to the various seed plants.

The compounds of the above described Examples 1 to 130 are applied in the above manner at dosages equivalent to 0.2, 1.0 and 5.0 kg of active agent/hectare of treated surface.

Herbicidal activity is observed, that is to say, significant damage to the test plants is observed.

TEST 2

Post-Emergence Greenhouse Treatment

A procedure similar to that of the pre-emergence test described above is followed, except that the 50 ml of herbicide solution is applied when the seed plants are at a 2-4 leaf stage. In order that uniform treatment of various seed plants may be effected at a time when each of the plant species has reached the 2-4 leaf stage, the various seed species are sown in time-staggered relationship.

Again the compounds according to Example 1 to 130 are applied in the above manner at dosages corresponding to 0.2, 1.0 and 5.0 kg of active agent. The determination of the herbicidal effect of the particular herbicide again involves a visual evaluation of the degree and quality of damage to the various seed plants.

In general, the herbicidal activity is stronger than obtained with the same compound at the same dosage rate according to Test 1.

TEST 3

The following Tables A and B will reflect a further evaluation of representative compounds of the formula I in the pre-emergence test procedure described in Test 1 at the rates of application indicated in the tables.

TABLE A

PRE-EMERGENCE APPLICATION 1 kg/ha

| Plant treated | Compound I Tested - % damage ||||||
|---|---|---|---|---|---|---|
| | Ex. 1 | Ex. 8 | Ex. 11 | Ex. 12 | Ex. 18 | Ex. 55 |
| Amaran. retrofl. | 90 | 100 | 100 | 100 | 70 | 100 |
| Capsella b.p. | 50 | 90 | 90 | 70 | 30 | 90 |
| Chenop. alb. | 20 | 60 | 80 | 50 | 70 | 40 |
| Galium aparine | 30 | 20 | 60 | 30 | 10 | 30 |
| Senecio vulg. | 10 | 50 | 70 | 20 | 80 | 60 |
| Stellaria media | 70 | 80 | 90 | 30 | 60 | 70 |
| Alfalfa | 0 | 50 | 90 | 30 | 30 | 70 |
| Bean | 0 | 20 | 20 | 0 | 0 | 30 |
| Carrot | 10 | 20 | 30 | 0 | 20 | 30 |
| Cotton | 0 | 0 | 0 | 0 | 10 | 0 |
| Flax | 20 | 80 | 80 | 60 | 90 | 90 |
| Potato | 0 | 10 | 10 | 10 | 10 | 0 |
| Soya | 0 | 80 | 80 | 30 | 0 | 20 |
| Sugar beet | 0 | 10 | 10 | 0 | 10 | 30 |
| Rape | 20 | 50 | 40 | 50 | 70 | 30 |
| Sunflower | 0 | 20 | 0 | 0 | 10 | 60 |
| Agropyron repens | 0 | 80 | 70 | 80 | 0 | 10 |
| Agrostis alba | 50 | 90 | 90 | 90 | 90 | 30 |
| Alopec. myos. | 30 | 90 | 90 | 90 | 80 | 70 |
| Apera sp. venti. | 30 | 80 | 90 | 70 | 80 | 80 |

TABLE A-continued

PRE-EMERGENCE APPLICATION 1 kg/ha

| Plant treated | Compound I Tested - % damage ||||||
|---|---|---|---|---|---|---|
| | Ex. 1 | Ex. 8 | Ex. 11 | Ex. 12 | Ex. 18 | Ex. 55 |
| Avena fatua | 10 | 90 | 90 | 80 | 60 | 10 |
| Echinochloa c.g. | 80 | 80 | 100 | 60 | 90 | 40 |
| Corn | 20 | 70 | 80 | 40 | 50 | 30 |
| Wheat | 10 | 30 | 30 | 50 | 10 | 10 |

TABLE B

PRE-EMERGENCE APPLICATION 5 kg/ha

| Plant treated | Compound I Tested - % damage ||||||
|---|---|---|---|---|---|---|
| | Ex. 1 | Ex. 8 | Ex. 11 | Ex. 12 | Ex. 18 | Ex. 55 |
| Amaran. retrofl. | 100 | 100 | 100 | 100 | 100 | 100 |
| Capsella b.p. | 70 | 100 | 100 | 90 | 100 | 90 |
| Chenop. alb. | 100 | 100 | 100 | 100 | 100 | 100 |
| Galium aparine | 80 | 80 | 90 | 80 | 90 | 30 |
| Senecio vulg. | 100 | 100 | 100 | 90 | 100 | 90 |
| Stellaria media | 100 | 100 | 100 | 90 | 100 | 90 |
| Alfalfa | 60 | 100 | 100 | 100 | 100 | 100 |
| Bean | 0 | 90 | 80 | 0 | 40 | 50 |
| Carrot | 50 | 70 | 90 | 40 | 70 | 10 |
| Cotton | 0 | 30 | 20 | 20 | 20 | 10 |
| Flax | 50 | 100 | 100 | 80 | 100 | 100 |
| Potato | 20 | 60 | 40 | 30 | 30 | 0 |
| Soya | 0 | 90 | 100 | 80 | 90 | 90 |
| Sugar beet | 20 | 60 | 70 | 20 | 80 | 70 |
| Rape | 50 | 100 | 100 | 100 | 100 | 80 |
| Sunflower | 0 | 50 | 40 | 20 | 50 | 10 |
| Agropyron repens | 10 | 90 | 80 | 100 | 90 | 30 |
| Agrostis alba | 100 | 90 | 90 | 90 | 90 | 100 |
| Alopec. myos. | 100 | 90 | 100 | 90 | 90 | 90 |
| Apera sp. venti. | 100 | 100 | 100 | 100 | 90 | 100 |
| Avena fatua | 80 | 90 | 100 | 90 | 90 | 30 |
| Echinochloa c.g. | 100 | 90 | 100 | 90 | 100 | 90 |
| Corn | 60 | 100 | 90 | 100 | 90 | 90 |
| Wheat | 40 | 90 | 90 | 70 | 80 | 30 |

The test results given in Tables A and B illustrate the good herbicidal effect of the compounds of formula I, especially against dicotyledoneous weeds, including *Galium aparine*, but also against grassy weeds, particularly against *Agrostis alba*, *Alopecurus myosuroides*, *Apera spica venti*, *Avena fatua* and *Echinochloa crus-galli*. The selective herbicidal activity is significant in i.a. sugar beet and wheat and particularly distinct in sunflower, potato and cotton.

TEST 4

Post-emergence Treatment

The following Tables C and D will reflect a further evaluation of representative compounds of the formula I in the post-emergence test procedure described in Test 2 at the rates of application indicated in the Tables.

TABLE C

POST-EMERGENCE APPLICATION 1 kg/ha

| Plant treated | Compound I Tested - % damage |||||||
|---|---|---|---|---|---|---|---|
| | Ex. 1 | Ex. 8 | Ex. 11 | Ex. 12 | Ex. 18 | Ex. 55 | Ex. 94 | Ex. 105 |
| Amaran. retrofl. | 100 | 90 | 80 | 100 | 100 | 90 | 100 | 90 |
| Capsella b.p. | 100 | 90 | 90 | 90 | 100 | 100 | 100 | 90 |
| Chenop. alb. | 100 | 30 | 30 | 60 | 80 | 80 | 90 | 80 |
| Galium aparine | 80 | 10 | 10 | 30 | 60 | 10 | 100 | 90 |
| Senecio vulg. | 30 | 30 | 50 | 40 | 50 | 100 | 90 | 100 |
| Stellaria media | 30 | 60 | 40 | 70 | 90 | 80 | 100 | 40 |
| Alfalfa | 80 | 20 | 50 | 10 | 40 | 60 | 40 | 30 |
| Bean | 30 | 60 | 90 | 70 | 90 | 100 | 100 | 40 |

TABLE C-continued

POST-EMERGENCE APPLICATION 1 kg/ha

Compound I Tested - % damage

| Plant treated | Ex. 1 | Ex. 8 | Ex. 11 | Ex. 12 | Ex. 18 | Ex. 55 | Ex. 94 | Ex. 105 |
|---|---|---|---|---|---|---|---|---|
| Carrot | 30 | 40 | 80 | 10 | 70 | 30 | 10 | 100 |
| Cotton | 90 | 80 | 50 | 90 | 70 | 50 | 100 | 90 |
| Flax | 100 | 90 | 70 | 90 | 100 | 100 | 90 | 30 |
| Potato | 30 | 10 | 30 | 20 | 40 | 10 | 30 | 20 |
| Soya | 10 | 80 | 70 | 90 | 90 | 100 | 90 | 20 |
| Sugar beet | 70 | 30 | 60 | 30 | 60 | 80 | 100 | 20 |
| Rape | 90 | 80 | 90 | 100 | 100 | 100 | 100 | 50 |
| Sunflower | 30 | 40 | 30 | 20 | 100 | 50 | 20 | 20 |
| *Agropyron repens* | 10 | 0 | 0 | 10 | 10 | 10 | 10 | 0 |
| *Agrostis alba* | 90 | 90 | 80 | 90 | 80 | 90 | 100 | 40 |
| *Alopec. myos.* | 80 | 70 | 60 | 90 | 40 | 90 | 30 | 10 |
| *Apera sp. venti.* | 30 | 70 | 80 | 80 | 40 | 50 | 30 | 10 |
| *Avena fatua* | 30 | 10 | 30 | 10 | 60 | 90 | 90 | 10 |
| *Echinochloa c.g.* | 100 | 80 | 60 | 90 | 90 | 100 | 80 | 10 |
| Corn | 60 | 10 | 30 | 20 | 40 | 50 | 20 | 10 |
| Wheat | 10 | 0 | 0 | 10 | 10 | 10 | 10 | 10 |

TABLE D

POST-EMERGENCE APPLICATION 5 kg/ha

Compound I Tested - % damage

| Plant treated | Ex. 1 | Ex. 8 | Ex. 11 | Ex. 12 | Ex. 18 | Ex. 55 | Ex. 94 | Ex. 105 |
|---|---|---|---|---|---|---|---|---|
| *Amaran. retrofl.* | 100 | 100 | 100 | 100 | 100 | 100 | 100 | 100 |
| *Capsella b.p.* | 100 | 100 | 100 | 100 | 100 | 100 | 100 | 100 |
| *Chenop. alb.* | 100 | 100 | 100 | 100 | 100 | 100 | 100 | 80 |
| *Galium aparine* | 100 | 40 | 100 | 80 | 100 | 100 | 100 | 90 |
| *Senecio vulg.* | 100 | 100 | 100 | 100 | 100 | 100 | 100 | 100 |
| *Stellaria media* | 100 | 100 | 100 | 100 | 100 | 100 | 100 | 80 |
| Alfalfa | 100 | 90 | 100 | 90 | 100 | 100 | 100 | 60 |
| Bean | 40 | 90 | 100 | 90 | 100 | 100 | 100 | 90 |
| Carrot | 100 | 100 | 100 | 100 | 100 | 80 | 100 | 100 |
| Cotton | 100 | 100 | 100 | 100 | 100 | 100 | 100 | 100 |
| Flax | 100 | 100 | 100 | 100 | 100 | 100 | 30 | 60 |
| Potato | 90 | 80 | 40 | 40 | 50 | 30 | 40 | 30 |
| Soya | 50 | 90 | 90 | 90 | 100 | 100 | 90 | 60 |
| Sugar beet | 100 | 100 | 100 | 100 | 100 | 100 | 100 | 80 |
| Rape | 100 | 100 | 100 | 100 | 100 | 100 | 100 | 90 |
| Sunflower | 70 | 100 | 80 | 90 | 100 | 100 | 80 | 40 |
| *Agropyron repens* | 20 | 10 | 20 | 20 | 60 | 20 | 10 | 10 |
| *Agrostis alba* | 100 | 90 | 100 | 90 | 100 | 100 | 100 | 30 |
| *Alopec. myos.* | 100 | 90 | 90 | 100 | 100 | 100 | 80 | 10 |
| *Apera sp. venti.* | 100 | 90 | 100 | 100 | 100 | 100 | 100 | 10 |
| *Avena fatua* | 100 | 50 | 50 | 90 | 100 | 90 | 80 | 40 |
| *Echinochloa c.g.* | 100 | 100 | 100 | 100 | 100 | 100 | 100 | 30 |
| Corn | 90 | 100 | 100 | 100 | 100 | 100 | 100 | 50 |
| Wheat | 40 | 40 | 30 | 50 | 30 | 20 | 10 | 10 |

The test results given in the Tables C and D illustrates the interesting activity against grasses, particularly against *Echinochloa crus-galli* (barn-yard grass), which is usually the main problem weed in paddy rice, and also against dicotyledoneous weeds after post-emergence application.

The selectivity against small grain crops, such as wheat, is significant.

TEST 5

Post-emergence Greenhouse Treatment (Rice culture)

A procedure similar to that of the post-emergence treatment of Test 2 is followed, except that the plants are standing in about 2 cm deep water and that the soil is a normally fertilized loamy soil.

In the following Table E a further evaluation of representative compounds of the formula I is given at the rates of application indicated in the Table.

TABLE E

| | % damage | |
|---|---|---|
| PLANT | Example 1 2 kg/ha | Example 32 1.2 kg/ha |
| Jagannath rice | 10 | 7 |
| JR-8 rice | 10 | 7 |
| Ipomaea | 3 | 17 |
| *Cyperus rotundus* | 10 | 0 |
| *Digitaria sanguinalis* | 97 | 8 |
| *Echinochloa crus-galli* (swiss origin) | 93 | 97 |
| *Echinochloa crus-galli* (italian origin) | — | 83 |
| *Panicum miliaceum* | 83 | 93 |
| Paspalum | — | 100 |
| *Setaria italica* | 93 | — |

— = not tested

What is claimed is:

1. A compound of formula I, $$X-CH_2-C=C-R_5 \atop R_3 \; R_4$$

(with $R_6$ and ring containing $R_1R_2N$, N, $CH_3$)

wherein
X is O or S
either
$R_1$ is $C_1-C_{18}$alkyl; $C_1-C_{18}$alkyl substituted by up to 2 substituents selected from $C_1-C_4$alkoxy or 2-tetrahydrofuryl; $C_3-C_8$cycloalkyl or $C_3-C_8$cycloalkyl-$C_1-C_5$alkyl unsubstituted or substituted by up to 2 halogens having an atomic weight of 9 to 35; or is $C_1-C_{18}$alkenyl and
$R_2$ is H or $C_1-C_5$alkyl,
or
$R_1$ and $R_2$ together are a $C_4-C_6$alkylene chain,
$R_3$ and $R_4$ and $R_5$ are each, independently H, Cl, Br or $C_1-C_4$alkyl and
$R_6$ is H or $C_1-C_5$alkyl,
with the proviso that at least one of $R_3$, $R_4$ and $R_5$ is halogen.

2. A compound of claim 1 of formula Ia, $$O-CH_2-C=C\genfrac{}{}{0pt}{}{R'_5}{R'_3 \; R'_4}$$

(with ring containing $R_1HN$, N, $CH_3$)

wherein
$R_1$ is as defined in claim 1,
$R_3'$ is H, Cl or Br,
$R_4'$ is H or $CH_3$
$R_5'$ is H, Cl or Br
whereby either $R_3'$ or $R_5'$ is Cl or Br.

3. A compound of claim 2 wherein $R_1$ is $C_1-C_{10}$alkyl.

4. The compound of claim 2 wherein $R_1$, $R_3'$, $R_4'$ and $R_5'$ are n-$C_6H_{13}$, Cl, H and H respectively.

5. The compound of claim 2 wherein $R_1$, $R_3'$, $R_4'$ and $R_5'$ are n-$C_6H_{13}$, H, $CH_3$ and Cl respectively.

6. A method of combatting weeds in a locus, which comprises applying to said locus a herbicidally effective amount of any one of the compounds of claims 1 to 5 in free base form or in agriculturally acceptable salt form.

7. The method of claim 6, in which the compound is applied at a rate of 0.2 to 7 kg per hectare.

8. A method of selectively combatting weeds in a desired crop locus, which comprises applying to the locus a compound of any one of claims 1 to 5 in an amount sufficient to severely damage or kill the weeds without substantially damaging the crop.

9. The method of claim 8 in which the compound is applied pre-emergence the weeds and wherein the crop locus is a small grain crop, sugar beet, potato, sunflower or cotton.

10. The method of claim 9, wherein the crop locus is cotton.

11. The method of claim 6, in which the compound is applied post-emergence the weeds and wherein the crop locus is a small grain crop.

12. The method of claim 11, wherein the crop locus is paddy rice.

13. The method according to any one of claims 10 to 12 in which the compound is applied at a rate of 0.5 to 5 kg per hectare.

14. A herbicidal composition comprising a compound of any one of claims 1 to 5 in free base form or in agriculturally acceptable salt form in association with herbicide carriers or diluents.

15. The compound of claim 2 wherein $R_1$ is isopenyl, $R_3'$ is Br, $R_4'$ is H and $R_5'$ is H.

16. The compound of claim 2 wherein $R_1$ is 1,3-dimethylbutyl, $R_3'$ is Cl, $R_4'$ is H and $R_5'$ is H.

17. The compound of claim 2 wherein $R_1$ is 1,3-dimethylbutyl, $R_3'$ is Br, $R_4'$ is H and $R_5'$ is H.

18. The compound of claim 2 wherein $R_1$ is 1,3-dimethylbutyl, $R_3'$ is H, $R_4'$ is H and $R_5'$ is Cl.

* * * * *